United States Patent [19]
Johnson et al.

[11] Patent Number: 6,083,919
[45] Date of Patent: Jul. 4, 2000

[54] MATERIALS AND METHODS FOR TREATING AUTOIMMUNE DISEASE

[75] Inventors: Howard M. Johnson; Mustafa G. Mujtaba, both of Gainesville, Fla.; Jeanne M. Soos, Waltham, Mass.

[73] Assignee: University of Florida, Gainesville, Fla.

[21] Appl. No.: 08/986,063

[22] Filed: Dec. 5, 1997

Related U.S. Application Data

[60] Provisional application No. 60/032,617, Dec. 5, 1996.

[51] Int. Cl.$^7$ ........................... A61K 38/00; A61K 38/21
[52] U.S. Cl. ............................. 514/21; 424/85.4
[58] Field of Search ............................. 514/21; 424/85.4

[56] References Cited

U.S. PATENT DOCUMENTS 5,650,396   7/1997   Canlino et al. ........................... 514/21

FOREIGN PATENT DOCUMENTS 9628183   9/1996   WIPO .

OTHER PUBLICATIONS

Stevens et al, J of Neuroimmunology (51) pp 77–83, 1994.

Rott et al, Eur J Immunol, vol. 24 pp 1434–40, 1994.

Schluesenen et al, J of Neuroimmulogy vol. 24, pp 249–58, 1989.

Soos et al, J immunology, vol. 155 pp 2747–53, 1995.

Karpus, W.J., Swanborg, R.H. (1991) "CD4+ suppressor cells inhibit the function of effector cells of experimental autoimmune encephalomyelitis through a mechanism involving transforming growth factor–β". Journal of Immunology 146: 1163–1168.

Weckmann, A.L., Alcocer–Varela, J. (1996) "Cytokine Inhibitors in Autoimmune Disease". Seminars in Arthritis and Rheumatism 26(2): 539–557.

Chen, Y. Inobe, J., Weiner, H.L. (1995) "Induction of Oral Tolerance to Myelin Basic Protein in CD8–Depleted Mice". Journal of Immunology 155: 910–916.

Reitamo, S. et al. (1994) "Interleukin 10 up–regulates elastin gene expression in vivo and in vitro at the transcription level". Biochemical Journal 302: 331–333.

Oswald, I.P. et al. (1992) "IL–10 synergizes with IL–4 and transforming growth factor–β to inhibit macrophage cytotoxic activity". Journal of Immunology 148: 3578–3582.

Vieira, P., de Waal Malefyt, R., Dang, M.–N., Johnson, K.E., Kastelein, R., Fiorentino, D.F., de Vries, J.E., Roncarolo, M.–G., Mosmann, T.R., and Moore, K.W. (1991) "Isolation and expression of human cytokine synthesis inhibitory factor cDNA clones: homology to Epstein–Barr virus open reading frame BCRF1" Proc. Natl. Acad. Sci. 88:1172.

Zamvil, S.S. and Steinman, L. (1990) "The T lymphocyte in experimental allergic encephalomyelitis" Annu. Rev. Immunol. 8:579–621.

Chaouat, G., Assal–Meliani, A., Martal, J., Raghupathy, R., Elliott, J., Mosmann, T. and Wegmann, T.G. (1995) "IL 10 prevents naturally occurring fetal loss in the CBA X DBA/2 mating combinations, and local defect in IL10 production in this abortion–prone combination is corrected by in vivo injection of IFNτ" J. Immunol. 154:4261–4268.

Johns, L.T., Flanders, K.C., Ranges, G.E. and Sriram, S. (1991) "Successful treatment of experimental allergic encephalomyelitis with transforming growth factor–β1" J. Immunol. 147:1792–1796.

Johnson, H.M. and Blalock, J.E. (1980) "Interferon immunosuppression: mediation by a suppressor factor" Infect. Immun. 29:301–305.

Massague, J. (1990) "The transforming growth factor–β family" Annu. Rev. Cell. Biol. 6: 597.

Moore, K.W., Vieira, P., Fiorentino, D.F., Trounstine, M.L., Khan, T.A., and Mosmann, T.R., (1990) "Homology of cytokine synthesis inhibitory factor (IL–10) to the Epstein–Barr virus gene BCRF1" Science 248:1230.

Rott, O., Fleischer, B. and Cash, E. (1994) "Interleukin–10 prevents experimental allergic encephalomyelitis in rats" Eur. J. Immunol 24: 1434–1440.

Schluesener, H.J. and Lider, O. (1989) "Transforming growth factors β1 and β2: Cytokines with identical immunosuppressive effects and potential role in the regulation of autoimmune T cell function" J. Neuroimmunol. 24:249–258.

Soos, J.M., Subramaniam, P.S., Hobeika, A.C., Schiffenbauer, J. and Johnson, H.M. (1995) "The IFN pregnancy recognition hormone, interferon tau, blocks both development and superantigen reactivation of experimental allergic encephalomyelitis without associated toxicity" J. Immunol. 155:2747–2753.

Stevens, D.B., Gould, K.E. and Swanborg, R.H. (1994) "Transforming growth factor–beta 1 inhibits tumor necrosis factor–alpha/lymphotoxin production and adoptive transfer of disease by effector cells of autoimmune encephalomyelitis" J. Neuroimmunol. 51: 77–83.

Primary Examiner—Russell Travers
Attorney, Agent, or Firm—Saliwanchik, Lloyd & Saliwanchik

[57] ABSTRACT

The subject invention pertains to novel methods for treating autoimmune–related diseases, such as Multiple Sclerosis (MS). One embodiment of the method of the invention comprises administering interleukin-10 (IL-10) and transforming growth factor-beta (TGF-β), in combination, to a person afflicted with or predisposed to an autoimmune disease. When administered in combination, these cytokines act in a synergistic manner as suppressor factors to inhibit the activation of self-reactive T cells that are involved in autoimmune disease.

20 Claims, 8 Drawing Sheets

MATERIALS AND METHODS FOR TREATING AUTOIMMUNE DISEASE

CROSS-REFERENCE TO RELATED APPLICATION

This application claims the benefit of U.S. Provisional Application Ser. No. 60/032,617, filed Dec. 5, 1996.

The subject invention was made with government support under a research project supported by National Institutes of Health Grant Nos. CA69959 and R37AI25904. The government has certain rights in this invention.

BACKGROUND OF THE INVENTION

Interferon tau (IFNτ) blocks the development of experimental allergic encephalomyelitis (EAE) in mice without associated toxicity; however, the mechanism of such action has not been fully elucidated (Soos et al., 1995). EAE is a murine model useful for studying the demyelinating disease multiple sclerosis (MS) (Zamvil and Steinman, 1990). Myelin basic protein (MBP) has been shown to be one of the primary central nervous system antigens responsible for induction of autoimmunity in the EAE model. Upon immunization with MBP, mice develop clinically observable tail and limb paralysis due to lymphocyte infiltration into the central nervous system accompanied by acute demyelination (Zamvil and Steinman, 1990).

The type I interferons (IFNs), α and β, have previously been shown to induce suppressor cells that block in vitro antibody production (Johnson and Blalock, 1980). Further, when type I IFNτ-induced suppressor cells were cultured in vitro, they were shown to produce a soluble factor that mediated immunosuppression. Past studies have suggested that "classic" T suppressor cells bear the CD8 phenotype. In addition, IFNτ-induced suppressor cell function occurs via a mechanism similar to that originally observed for type I IFNα and β inhibition of antibody production in vitro.

A suppressor mechanism shared by the type I IFNs is the induction of soluble suppressor factors. The identification of the cytokines responsible for the induction of suppressor cells useful in the treatment of autoimmune diseases is provided by the subject invention. Surprisingly, these cytokines act in a synergistic fashion. Although IL-10 (Vieira et al., 1991; Moore et al., 1990) and TGF-β (for a review see Massague, 1990) have previously been shown to inhibit events associated with autoimmune disease (Chaouat et al., 1995; Rott et al., 1994; Stevens et al., 1994; Johns et al., 1991; Schluesener and Lider, 1989), it was not known that these cytokines are produced by suppressor cells involved in prevention of EAE, nor was the synergistic action of these cytokines or self-reactive T cells known.

BRIEF SUMMARY OF THE INVENTION

The subject invention concerns novel methods for treating autoimmune-related diseases, such as Multiple Sclerosis (MS). The method of the subject invention comprises administering the cytokines interleukin-10 (IL-10) and transforming growth factor-beta (TGF-β), in combination, to a person afflicted with, or predisposed to, an autoimmune disease. When administered in combination, IL-10 and TGF-β act as suppressive cytokines in a synergistic manner to inhibit the activation of self-reactive T cells in autoimmune diseases. In a further embodiment of the subject method, IL-10 and TGF-β can be administered in conjunction with IFNτ.

DETAILED DESCRIPTION OF THE INVENTION

Figure 1:
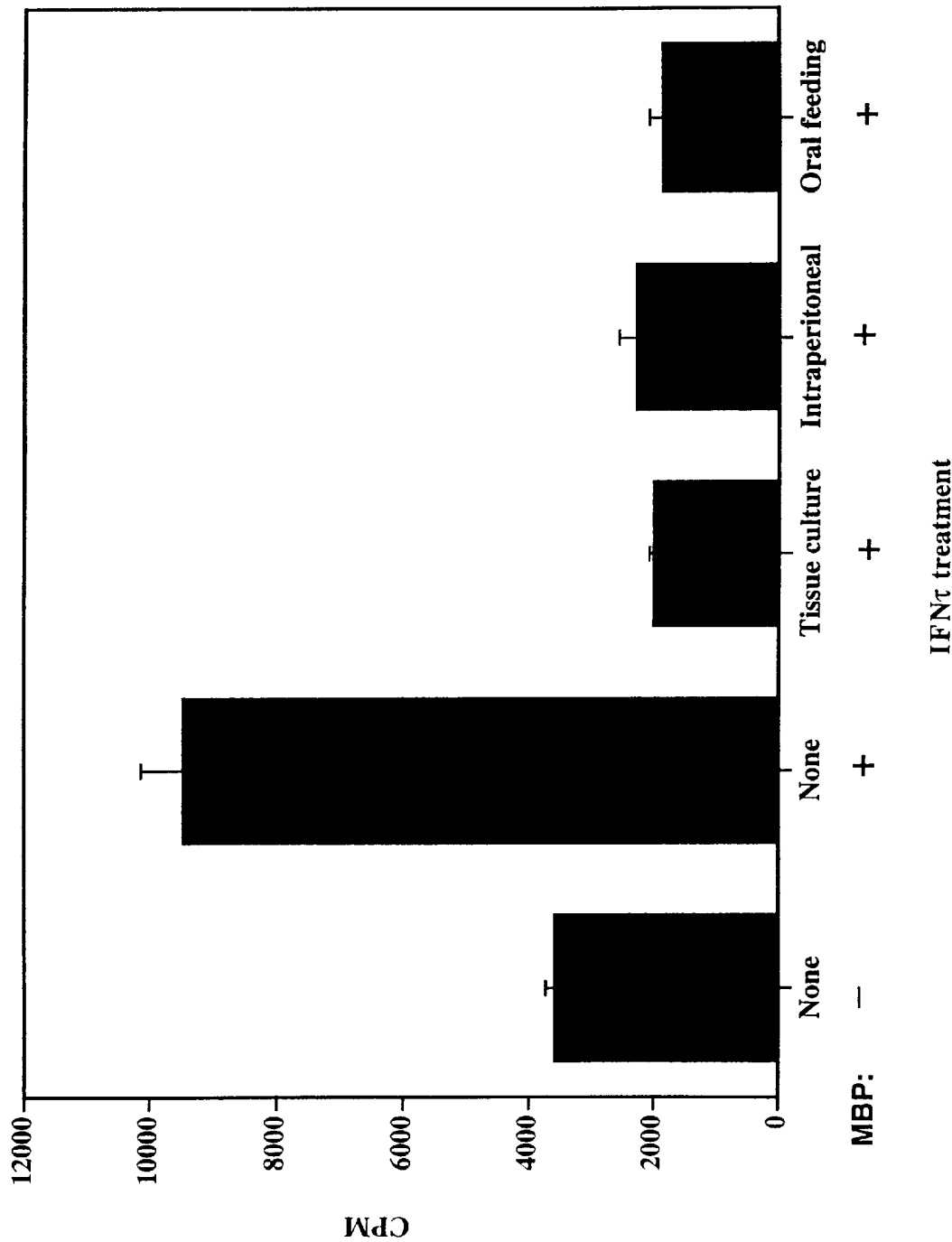
FIG. 1. IFNτ-treated spleen cells inhibit MBP-specific T cell proliferation. Suppressor cells were induced with IFNτ both in vitro and in vivo. IFNτ-treated spleen cells were washed and co-cultured at $1.0 \times 10^5$ cells/well with MBP-specific mouse spleen cells ($2.5 \times 10^5$ cells/well) and MBP protein at 100 μg/ml for 96 h. Media-treated spleen cells served as controls. Data from one of three representative experiments are presented as mean CPM±S.D. of quadruplicate cultures. Proliferation was measured by [$^3$H]-thymidine incorporation. IFNτ suppressor cells induced by all three methods showed significant suppression by $X^2$ test with p<0.001 relative to MBP-stimulated controls.

The subject invention concerns novel therapeutic and prophylactic methods for treating autoimmune-related diseases, such as Multiple Sclerosis (MS). In one embodiment of the subject method, an effective amount of the cytokines IL-10 and TGF-β are administered to a person afflicted with, or predisposed to, an autoimmune disease. Preferably, IL-10 and TGF-β are administered to a patient in combination or in a therapeutically effective order. The methods of the invention can induce stable remission of disease in a patient. These cytokines function in a synergistic manner to suppress autoimmune related immune responses.

The subject invention also concerns methods for inhibiting T cell responses associated with autoimmune diseases. In one embodiment, T cell responses, such as T cell activation, proliferation or cytokine production, can be inhibited in a synergistic manner by administering an effective amount of IL-10 and TGF-β to an animal. As exemplified herein, MBP specific T cell responses, such as activation and proliferation, are inhibited in an animal by administering IL-10 and TGF-β. Thus, the methods of the subject invention can be used to inhibit pathological T cell responses in an animal having an autoimmune disorder.

Treatment of a patient with IL-10 and TGF-β according to the methods of the present invention can also be used to inhibit the humoral arm of the immune system. Thus, the methods of the subject invention can also be used to inhibit B cell responses, such as antigen specific B cell activation and antibody production, in autoimmune diseases. For example, the present invention can be used to inhibit anti-MBP antibody and MBP-specific B cell effects in EAE in mice and other animals, and in multiple sclerosis in humans.

The subject invention can also be used to prevent or reduce activation of microglia and lymphocytic infiltration into the central nervous system that can be associated with certain autoimmune diseases, such as multiple sclerosis.

It has been determined that IFNτ downregulates the expression of MHC class II molecules on lymphocytes. Accordingly, in another embodiment of the present method, an effective amount of IL-10 and TGF-β is administered along with IFNτ in a patient.

The IL-10, TGF-β and IFNτ used with in the methods of the present invention can be produced either by natural or recombinant means. These cytokines can be of mammalian origin. Preferably, the cytokines are human IL-10, TGF-β and IFNτ. Biologically active muteins (mutated proteins) of the cytokines, as well as other molecules, such as fragments, peptides and variants, that possess substantially the same bioactivity as the subject cytokines, are contemplated within the scope of the subject methods. For example, IL-10, TGF-β, and IFNτ polypeptides that contain amino acid substitutions, insertions, or deletions that do not substantially decrease the biological activity and function of the mutant polypeptide in comparison to native polypeptide is within the scope of the present invention.

Therapeutic application of the subject cytokines and compositions containing them can be accomplished by any suitable therapeutic method and technique presently or prospectively known to those skilled in the art. The cytokines can be administered by any suitable route known in the art including, for example, oral, parenteral, subcutaneous, or intravenous routes of administration. Administration of the cytokines of the invention can be continuous or at distinct intervals as can be determined by a person skilled in the art.

The compounds of the subject invention can be formulated according to known methods for preparing pharmaceutically useful compositions. Formulations are described in detail in a number of sources which are well known and readily available to those skilled in the art. For example, *Remington's Pharmaceutical Science* by E. W. Martin describes formulations which can be used in connection with the subject invention. In general, the compositions of the subject invention will be formulated such that an effective amount of the bioactive cytokine(s) is combined with a suitable carrier in order to facilitate effective administration of the composition.

The compositions used in present method may also be in a variety of forms. These include, for example, solid, semi-solid, and liquid dosage forms, such as tablets, pills, powders, liquid solutions or suspension, suppositories, injectable and infusible solutions. The preferred form depends on the intended mode of administration and therapeutic application. The compositions also preferably include conventional pharmaceutically acceptable carriers and adjuvants which are known to those of skill in the art.

The compounds of the subject invention may also be administered utilizing liposome technology, slow release capsules, implantable pumps, and biodegradable containers. These delivery methods can, advantageously, provide a uniform dosage over an extended period of time.

Examples of carriers or diluents for use with the subject cytokines include ethanol, dimethyl sulfoxide, glycerol, silica, alumina, starch, and equivalent carriers and diluents. To provide for the administration of such dosages for the desired therapeutic treatment, new pharmaceutical compositions of the invention will advantageously comprise between about 0.1% and 45%, and especially, 1 and 15% by weight of the total of one or more of the cytokines based on the weight of the total composition including carrier or diluent.

As specifically exemplified herein, IFNτ induces CD4 T cells to become suppressor cells in NZW mice by oral administration or intraperitoneal injection of IFNτ, and by treatment of mouse spleen cells with IFNτ in tissue culture. The suppressor cells inhibit MBP stimulation of spleen cells from MBP-immunized mice, and protect mice against induction of EAE. In addition, the CD4 T suppressor cells produce both IL-10 and TGF-β, which act synergistically to inhibit MBP-specific T cell proliferation. Induction of suppressor cells can be blocked by pretreatment, but not post-treatment, of IFNτ with neutralizing antibodies, thus establishing that induction of suppressor cells is specific for IFNτ, but that the inducer of suppressor cells is not itself IFNτ. Therefore, IFNτ inhibition of EAE appears to occur via induction of suppressor cells and their suppressor factors.

The induction of suppressor cells is not unique to IFNτ, as IFNβ also induced suppressor cells in spleen cell cultures. Further, the dose response curves for the two IFNs were similar. Also, these suppressor cells produce suppressor factors that inhibit MBP stimulation of EAE spleen cells. Thus, type I IFNs may, in general, protect against autoimmune diseases such as MS by induction of suppressor cells and suppressor factors.

As indicated above, IFNτ protected mice against EAE when administered orally even though relatively little IFNτ was found in the circulation. The gut is lined with over half of the cells of the immune system. The suppressor cells induced by oral IFNτ administration must be mobile, since the autoreactive MBP-specific T cells that are inhibited are themselves mobile, and in fact migrate to the central nervous system to cause EAE in the absence of IFNτ treatment. IFNτ treated mice that are immunized with MBP show little or no lymphocyte infiltration of the CNS.

The CD4 T suppressor cell induced is most likely the Th2 type based on the detection of TGF-β and IL-10 in suppressor cell supernatants. Further, since this suppressor cell is induced by IFNτ and probably also by other type I IFNs in the absence of MBP, it is most likely to be antigen-nonspecific in its effect. In fact, preliminary data suggest that suppressor cell supernatant inhibits mitogen stimulation of mouse spleen cells, and superantigen induced effects were similarly suppressed by CD4 T suppressor cells and their supernatant via IL-10 and TGF-β. There was no evidence that non-CD4 T cells, including CD8 cells, possessed suppressor cell activity. This observation is in contrast to some other studies on suppressor cells (Nouri et al., 1991; Mukasa et al., 1994; Blank et al., 1995; Castedo et al., 1993). Other studies have also shown that the immune response is suppressed by antigen-specific CD4 Th2 cells (Karpus and Swanborg, 1991; Nabozny et al., 1991; Martinotti et al., 1995; Smith et al., 1991).

One aspect of the subject invention pertains to the discovery that CD4 suppressor T cells produce both IL-10 and TGF-β that acted synergistically to inhibit MBP stimulation of spleen cells from EAE mice. IL-10 was detected in sera of mice which received prolonged i.p. injections or prolonged oral feeding of IFNτ. Also demonstrated herein is the discovery that IFNτ-induced suppressor cells produce IL-10 and TGF-β to synergistically inhibit MBP-specific T cell proliferation.

The subject invention also pertains to methods for inhibiting B cell responses, such as B cell activation or B cell antibody production, by contacting a B cell with an effective amount of IL-10 and TGF-β. The invention also concerns methods for inhibiting a T cell response, such as antigen specific T cell proliferation or activation, by contacting a T cell with an effective amount of IL-10 and TGF-β.

The subject invention also concerns novel compositions comprising IL-10 and TGF-β, or biologically active muteins, fragments or variants thereof. Preferably, a composition of the invention comprises purified IL-10 and TGF-β. More preferably, a purified composition is provided in a pharmaceutically acceptable carrier or excipient.

The subject invention also concerns kits comprising IL-10 and TGF-β in one or more compartments. The kits can be used in practicing the methods of the invention. Preferably, the kits comprise purified IL-10 and TGF-β compositions in a pharmaceutically acceptable carrier or excipient.

As used herein, the term "TGF-β" includes all types of TGF-β including TGF-β1, TGF-β2 and TGF-β3.

All references cited herein are hereby incorporated by reference.

Materials and Methods

IFNs.

The ovine IFNτ (IFNτ) gene was expressed in *Pichia pastoris* using a synthetic gene construct (Heeke et al., 1996). IFNτ was secreted into the medium and was purified by successive DEAE-cellulose and hydroxylapatite chromatography to electrophoretic homogeneity as determined by SDS-PAGE and silver staining analysis. The purified protein had a specific activity of 2.9 to $4.4 \times 10^7$ U/mg protein as measured by antiviral activity using a standard viral microplaque reduction assay on MDBK cells (Pontzer et al., 1991). MuIFNβ (specific activity $4.1 \times 10^7$ U/mg) was obtained from Lee Biomolecular (San Diego, Calif.).

Antibodies and cytokines.

Monoclonal rat anti-mouse IL-10, recombinant mouse IL-10, and monoclonal mouse anti-TGF-$\beta_1$, anti-TGF-$\beta_2$, and anti-TGF-$\beta_3$ were obtained from Genzyme, Cambridge, Mass. Ultrapure natural human TGF-$\beta_1$, which shows cross-reactivity in most mammalian cell types, was also obtained from Genzyme. A 1:10 dilution of HL100, a monoclonal antibody specific for IFNτ, was used to neutralize 5000 U/ml of IFNτ prior to usage. All antibodies and cytokines were used in proliferation assays as described herein.

Interferon induction of suppressor cells.

Suppressor cells were induced both in vitro and in vivo. For in vitro induction, NZW mouse spleen cells ($5.0 \times 10^7$/ml) were incubated with 5000 U/ml of IFNτ for 24 h at 37° C., after which the cells were washed twice prior to use. In vivo induction of suppressor cells in naive NZW mice involved administration of a single dose of IFNτ ($10^5$ U) either intraperitoneally (i.p.) or by oral feeding with PBS used as the vehicle for administration. After 24 h, mice were sacrificed and the spleens removed. Spleen cells were washed and resuspended in RPMI 1640 medium supplemented with 2% fetal bovine serum and used as described below.

Induction of EAE.

For induction of EAE, 300 μg of bovine MBP (MBP) were emulsified in complete Freund's adjuvant (CFA) containing 8 mg/ml H37Ra (*Mycobacterium tuberculosis*, Difco, Detroit, Mich.) and injected into two sites at the base of the tails of NZW mice. On the day of immunization and 48 h later, 400 ng of pertussis toxin (List Biologicals, Campbell, Calif.) were also injected. Mice were clinically examined daily for signs of EAE, and severity of disease was graded using the following scale: 1) loss of tail tone; 2) hind limb weakness, 3) paraparesis, 4) paraplegia; 5) moribund/death.

Adoptive transfer of suppressor cells.

Suppressor cells were induced in vitro with IFNU as described above and resuspended in phosphate buffered saline (PBS). NZW mice were injected intraperitoneally with 100 μl of PBS containing $5 \times 10^6$ suppressor cells 48 h before, on the day of, and 48 h after immunization with MBP for induction of EAE. Mice were examined daily for signs of EAE, and the severity of disease was graded as noted above.

CD4 T cell isolation and depletion.

CD4 T cells effects were examined using both positive and negative CD4 T cell selection processes. The Cellect-plus mouse CD4 kit (Biotex Laboratories, Inc., Alberta, Canada), an immunoaffinity column, was used to isolate CD4 cells from NZW mouse spleen lymphocyte cultures treated with media or IFNτ. Depletion of CD4 T cells from mouse spleen lymphocyte cultures treated with IFNτ or media was carried out using rat anti-mouse L3/T4 CD4 monoclonal antibody (Biosource International, Camarillo, Calif.) and Low-Toxic-M rabbit complement (Accurate Chemical and Scientific Corporation, Westbury, N.Y.). Lymphocytes from NZW mouse spleen were resuspended at $10^7$ cells/ml in RPMI 1640 medium and incubated with 1:10 dilution of anti-mouse L3/T4 CD4 antibody for 1 h at 4° C. Cells were then centrifuged and resuspended in 1:10 dilution of rabbit complement in RPMI 1640 medium for 1 h at 37° C. The cultures were washed and used for further experimentation.

Production of suppressor factor.

Suppressor cells were generated in vitro by incubating spleen cells with 5000 U/ml of IFNτ for 24 h at 37° C. as described above. Cells were then washed and resuspended at $10^8$ cells/ml in fresh culture medium. After incubating for an additional 2 h at 37° C., clarified supernatants were collected and tested for suppressor activity.

Proliferation assay.

Spleen cells from MBP-immunized NZW mice (2.5–5.0× $10^5$ cells/well) were co-cultured with IFNτ or IFNβ-induced suppressor cells (1.0–5.0×$10^5$/well), suppressor cell supernatants, or IL-10 and TGF-β in the presence of 30 or 100 μg/ml of MBP. Suppressor cell supernatants were also pretreated for 2 h with either anti-IL10 antibody (25 μg/ml) or anti-TGF-β antibody (25 μg/ml) and then cultured with MBP-specific cells in the presence of MBP. Cultures were incubated for 96 h at 37° C. The cultures were then pulsed with [$^3$H]-thymidine (1.0 μCi/well; Amersham, Indianapolis, Ind.) 18 h before harvesting onto filter paper discs using a cell harvester. Cell-associated radioactivity was quantified using a β-scintillation counter. Stimulation index was determined by dividing experimental CPM by control (unstimulated) CPM.

Following are examples which illustrate procedures for practicing the invention. These examples should not be construed as limiting. All percentages are by weight and all solvent mixture proportions are by volume unless otherwise noted.

EXAMPLE 1

IFNτ-treated spleen cells inhibit MBP-specific T cell proliferation

Spleen cells were treated with IFNτ in tissue culture or were obtained from mice injected intraperitoneally (i.p.) with IFNτ, or from mice treated orally with IFNR. IFNτ-treated spleen cells from all three sources inhibited MBP induced proliferation of spleen cells from EAE mice by as much as 80% relative to the control response (FIG. 1). Similar to type I IFN induction of suppressor cells for antibody production (Johnson and Blalock, 1980), IFNτ suppressed MBP-specific immune response via induction of suppressor cells. It was also determined that the induction of suppressor cells by IFNτ is dose-dependent.

EXAMPLE 2

IFNτ suppressor cells protect mice against EAE

Figure 2:
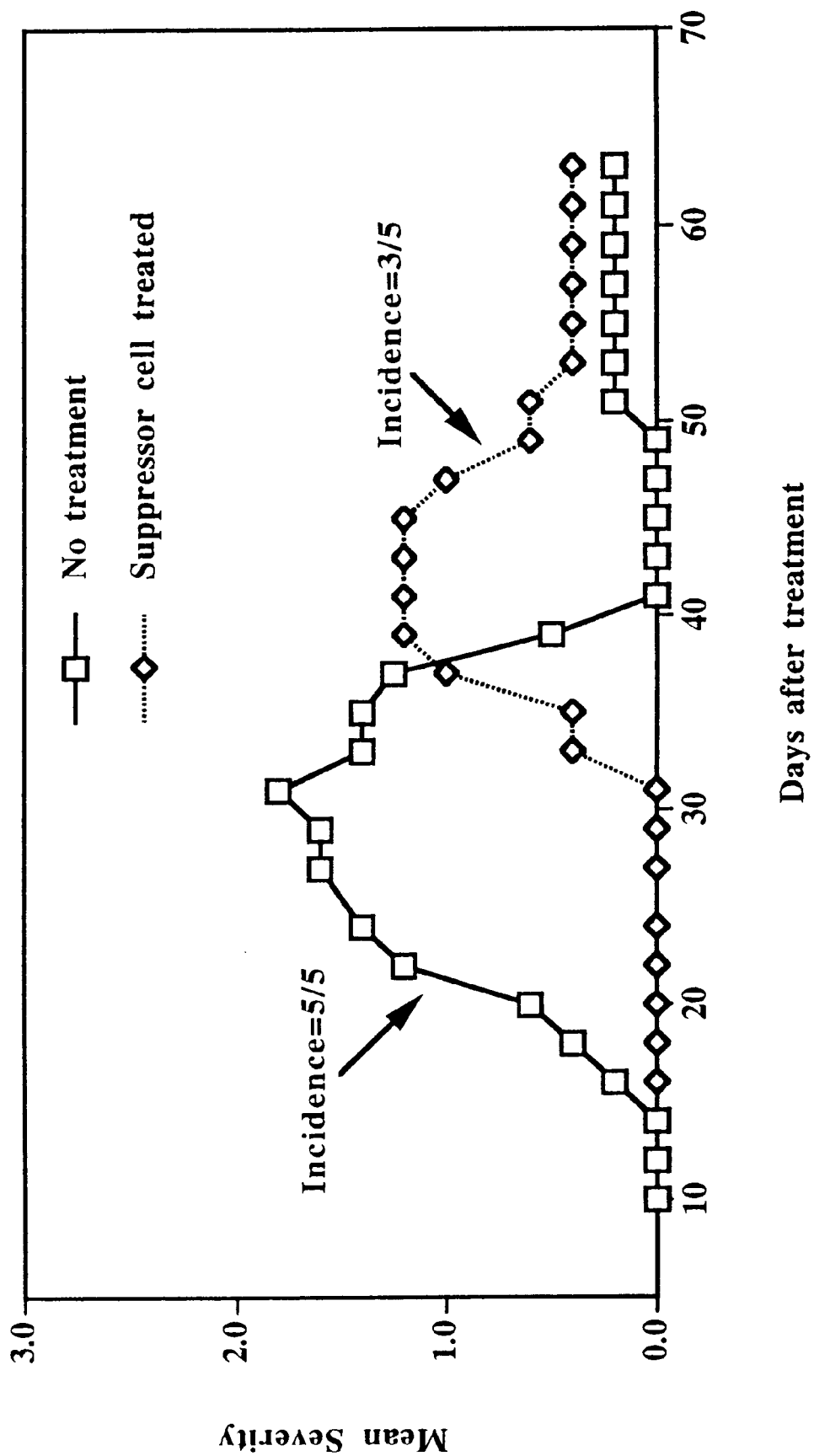
FIG. 2. IFNτ-induced suppressor cells can delay the onset of EAE in mice. NZW mice were injected i.p. with IFNτ-treated whole spleen cells ($5 \times 10^6$) 48 h before, on the day of, and 48 h after immunization with bovine MBP for induction of EAE. Mice were followed daily for signs of EAE, and mean severity of paralysis for each group was graded based on the scale mentioned in the materials and methods. Control mice had an average severity of 2.8, while adoptive transferred mice had a severity of 2.0. Mean day of onset of paralysis for the control and suppressor cell-treated mice were 19.6±2.6 and 34.3±2.3 days, respectively. The delay of onset of paralysis was statistically significant as shown by student's t-test (p<0.001).

Adoptive transfer of IFN—induced suppressor cells to NZW mice immunized with bovine MBP was carried out in order to determine if the suppressor cells protected the mice from development of EAE. NZW mice have previously been shown to be susceptible to development of EAE after immunization with either rat MBP (Zamvil et al., 1994; Kumar et al., 1994) or bovine MBP. Others have shown the transfer of peripheral cells from orally administered IFN donor mice to recipient mice causes suppression of white blood cells (Fleischmann et al., 1992). Suppressor cells induced in culture with IFNτ were injected i.p. 48 h before, at the time of, and 48 h after immunization of mice with MBP. Suppressor cell-treated mice showed delayed onset of EAE (34.3 days) compared to untreated controls (19.6 days), and the incidence of EAE was 3 of 5 with lower severity of disease for suppressor cell-treated mice compared to 5 of 5 with higher severity of disease for untreated mice (FIG. 2). Thus, adoptive transfer of IFNτ induced suppressor cells significantly protected mice against EAE.

EXAMPLE 3

IFNτ-induced suppressor cells are CD4 T cells

Figure 3:
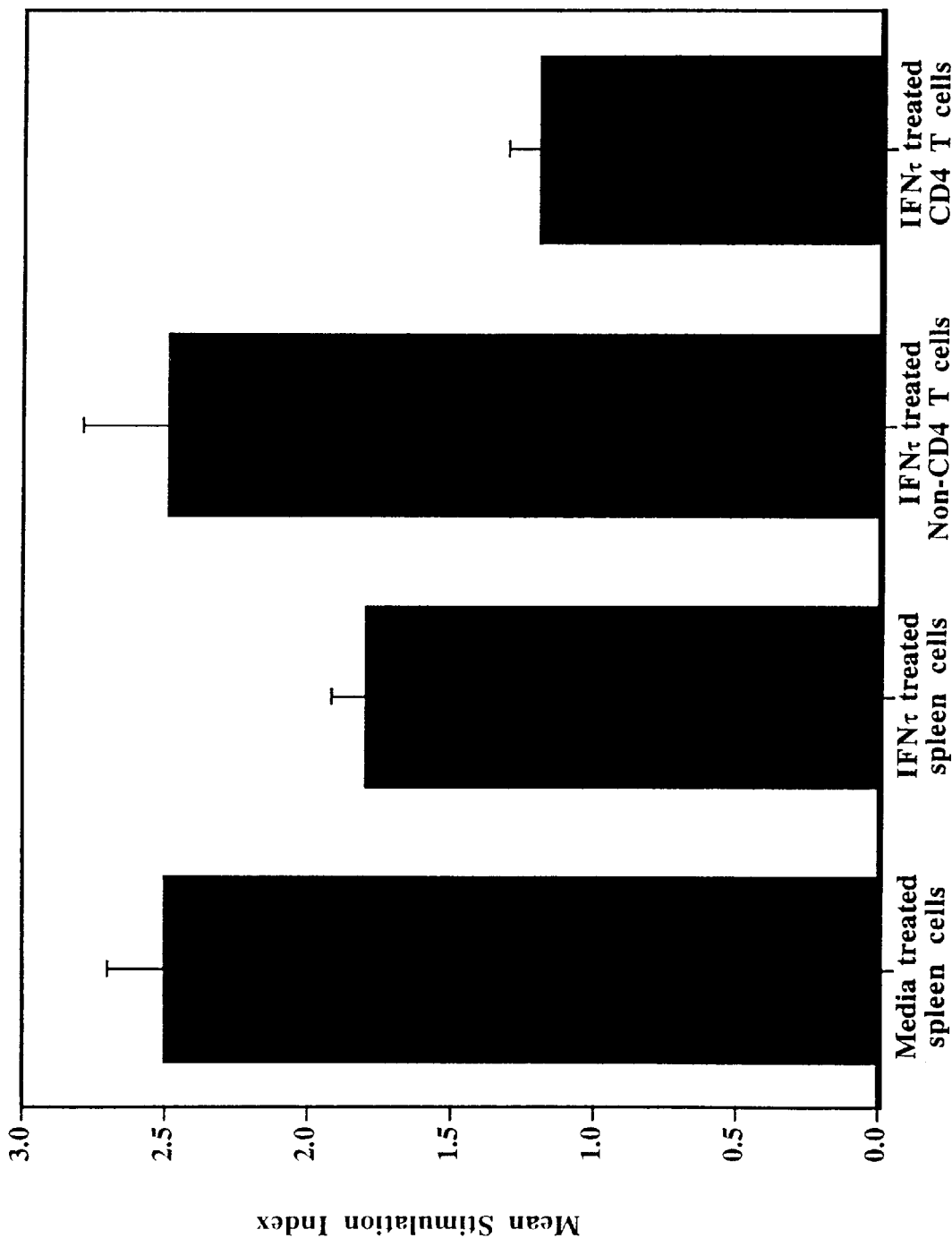
FIG. 3. IFNτ-induced suppressor cells are CD4 T cells. NZW mouse spleen cells were treated with media or IFNτ for 24 h in vitro. CD4 T cells were isolated from IFNτ-treated cell cultures using an immunoaffinity column. CD4 T cells were depleted from a second set of IFNτ-treated cells using anti-CD4 antibody plus complement. Whole and fractionated spleen cells ($2.5 \times 10^5$) were co-cultured with MBP-specific cells ($2.5 \times 10^5$ cell/well) in the presence of 30 μg/ml of MBP. Proliferation was measured by [$^3$H]-thymidine incorporation. Data from one of two representative experiments are presented as mean stimulation index±S.D. of quadruplicate cultures. Co-cultures of MBP-specific cells and fractionated media-treated cells had similar stimulation indices as those with whole unfractionated cells. Statistical significance by $X^2$ test for CD4 T cell suppression was p<0.001 relative to the media treated spleen cell control. The CPM for unstimulated cells were 1003±183.

The phenotype of the suppressor cells was determined by using antibody affinity columns to purify CD4 T cells and using specific CD4 antibody and complement to deplete CD4 T cells from IFNτ-treated cultures (FIG. 3). CD4 T cells purified from an IFNτ-treated spleen cell preparation inhibited MBP-specific T cell responses by almost 50%, while non-CD4 T cultures from IFNτ treated spleen cells were without effect. The non-CD4 T cell preparations consisted of CD8 T cells, macrophages, and other cells. Thus, the suppressor cell appears to be a CD4 T cell.

EXAMPLE 4

Suppressor cells produce soluble suppressor factor(s)

Figure 4A:
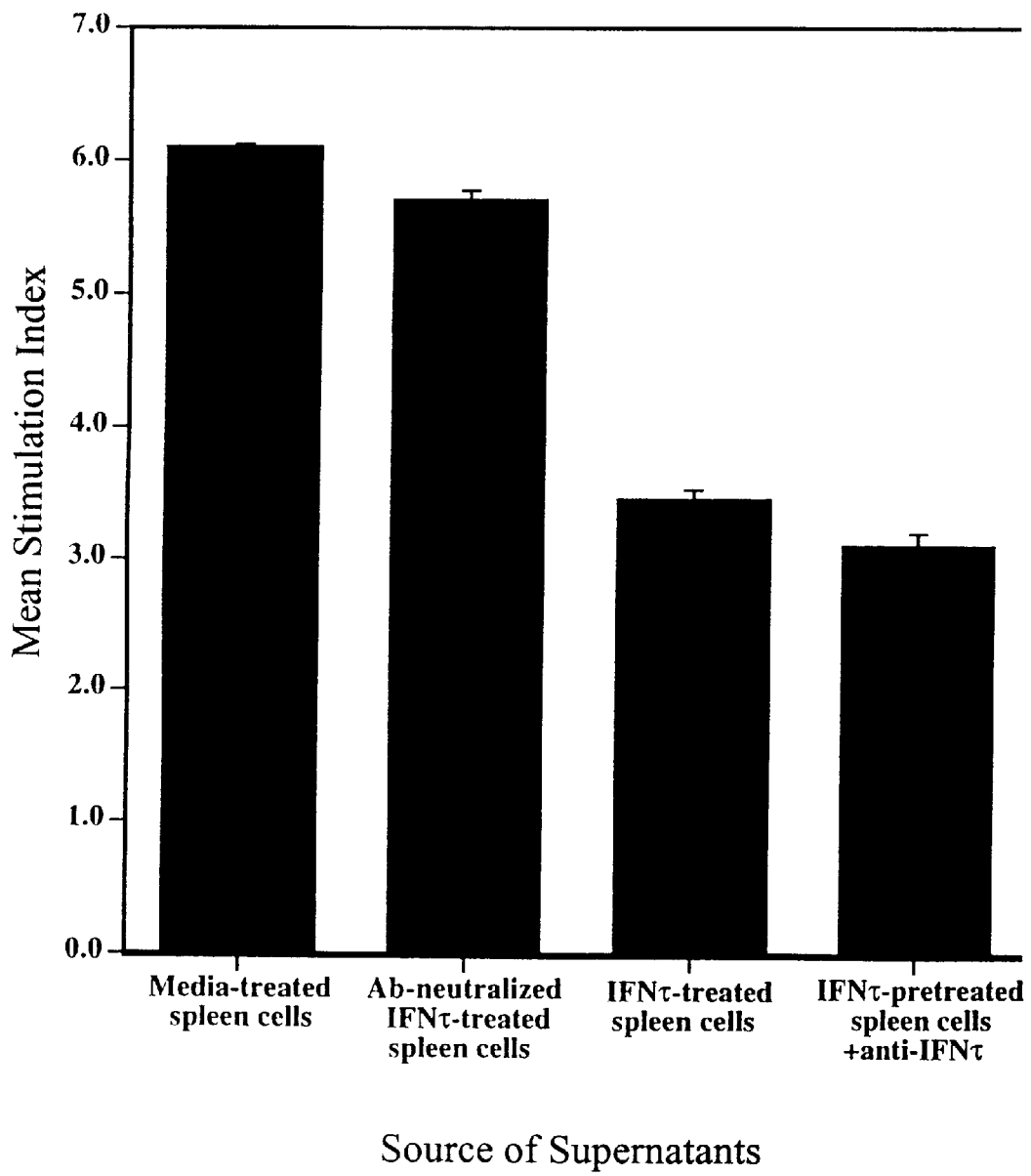
FIGS. 4A and B show supernatant sources IFNτ-induced CD4 T suppressor cells produce soluble suppressor factor(s). NZW mouse spleen cells were treated with media or with 5000 U/ml IFNτ in the presence and absence of neutralizing antibody to IFNτ (mAb HL-100) (FIG. A). CD4 T cells were isolated from media and IFNτ-treated cultures (FIG. B). After washing, the cells were incubated for 2 h in media, and supernatants were collected. Supernatants were incubated with MBP-specific mouse spleen cells ($5.0 \times 10^5$ cells/well) in the presence of 30 μg/ml of MBP protein. Proliferation was measured by [$^3$H]-thymidine incorporation. Data from one of two representative experiments are presented as mean stimulation index±S.D. of quadruplicate cultures. In FIG. A, statistical significance by $X^2$ test for suppressive activity of supernatants from cells pretreated with IFNτ was p<0.001. In FIG. B, statistical significance by $X^2$ test for suppressive activity of supernatants from CD4 T cells pretreated with IFNτ was p<0.001. The CPM for the unstimulated cells were 138±36 in FIG. A and 262±52 in FIG. B.
Figure 4B:
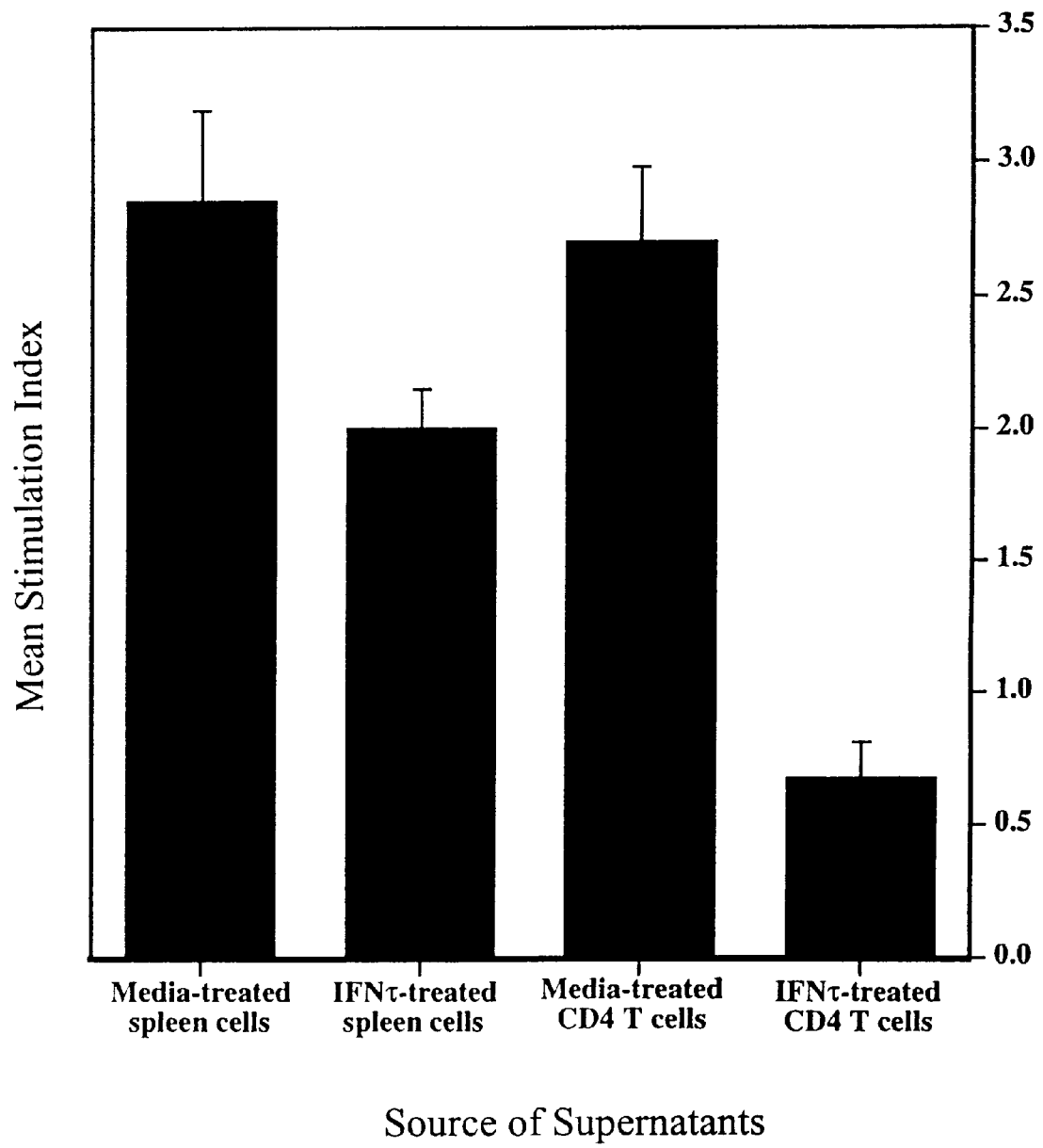

IFNτ-treated cells were examined for production of a suppressor factor. As shown in FIG. 4A, supernatants from IFNτ-treated spleen cells that had been incubated for 2 h at 37° C. inhibited MBP-specific T cell responses. Inhibitory supernatants were not produced by cells treated with IFNτ that had been neutralized with specific antibody prior to treatment of cells. Further, the antibodies did not inhibit suppressor cell activity when added to cells after treatment with IFNτ. Consistent with the CD4 T cell phenotype of the suppressor cell, supernatants from IFNτ-treated CD4 T cells suppressed the MBP-specific responses (FIG. 4B). Thus, the IFNτ induced CD4 suppressor T cell produces soluble suppressor factor(s).

EXAMPLE 5

IFNτ induced suppressor cells produce IL-10 and TGF-β

Figure 5A:
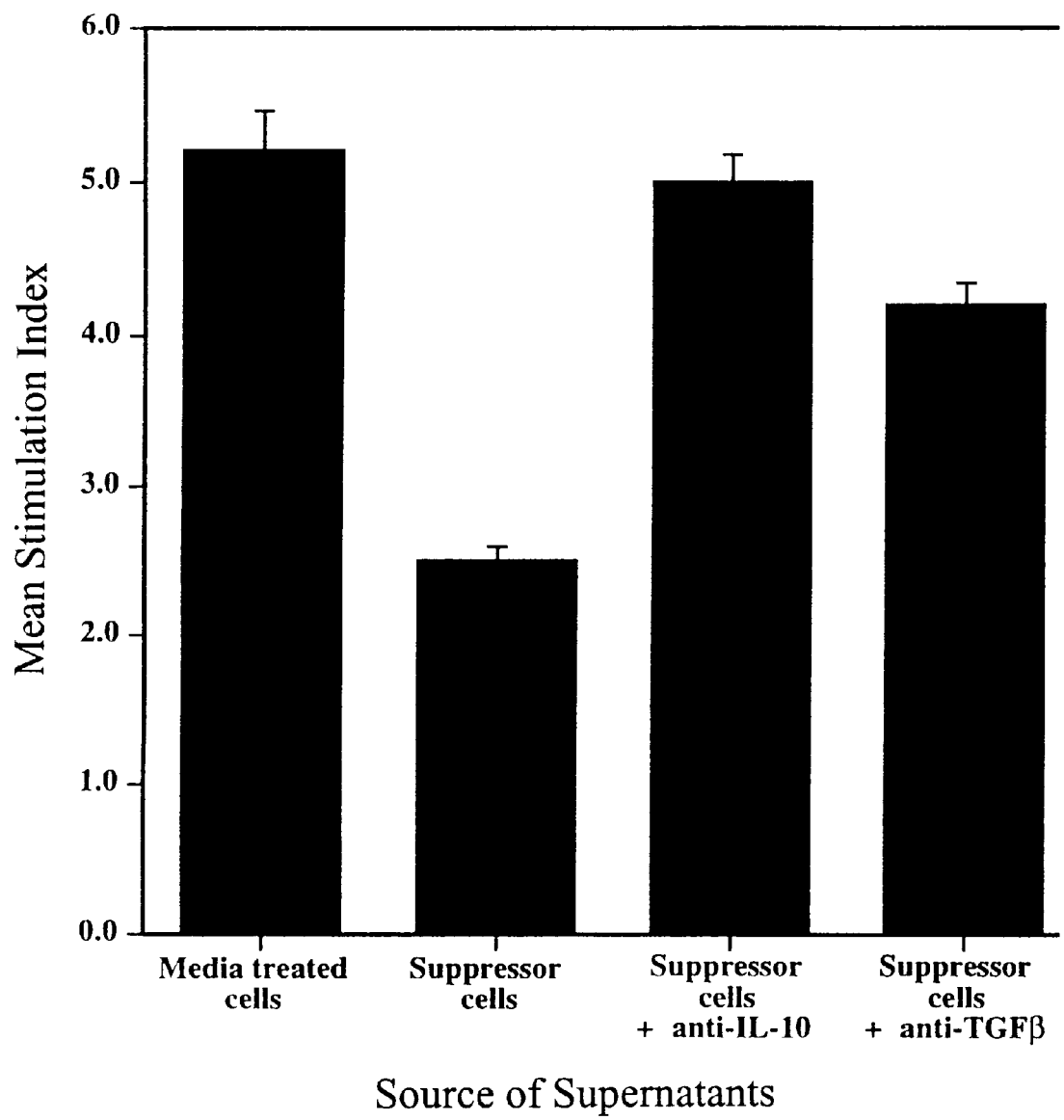
FIGS. 5A and B show supernatant sources. Blockage of IFNτ induced suppressor cell and suppressor supernatant effects on MBP stimulation of sensitized EAE mouse spleen cells with monoclonal antibodies to IL-10 and TGF-β. Media-treated spleen cells and suppressor spleen cells ($3.09 \times 10^5$ cells/well) induced in vitro with IFNτ (FIG. A) and their supernatants (FIG. B) were each co-cultured with MBP-sensitized spleen cells ($5 \times 10^5$ cells/well) in the presence of 30 μg/ml of MBP. Anti-IL-10 (25 μg/ml) and anti-TGF-β (25 μg/ml) antibodies were added at initiation of cultures. Proliferation was assessed after 96 h by [$^3$H]-thymidine incorporation. Data from one of two representative experiments are presented as mean stimulation index±S.D. of quadruplicate cultures. The effects of anti-IL-10 and anti-TGF-β antibodies on media treated cells were similar to those of media controls shown. In FIG. A, blockage of the suppressive activity of the suppressor cells by both antibodies were statistically significant p<0.001) as determined by the $X^2$ test. In FIG. B, blockage of the suppressive activity of the suppressor cell supernatant by both antibodies was statistically significant (p<0.001) as determined by the $X^2$ test. The CPM for the unstimulated cells were 4843±18 in FIG. B.
Figure 5B:
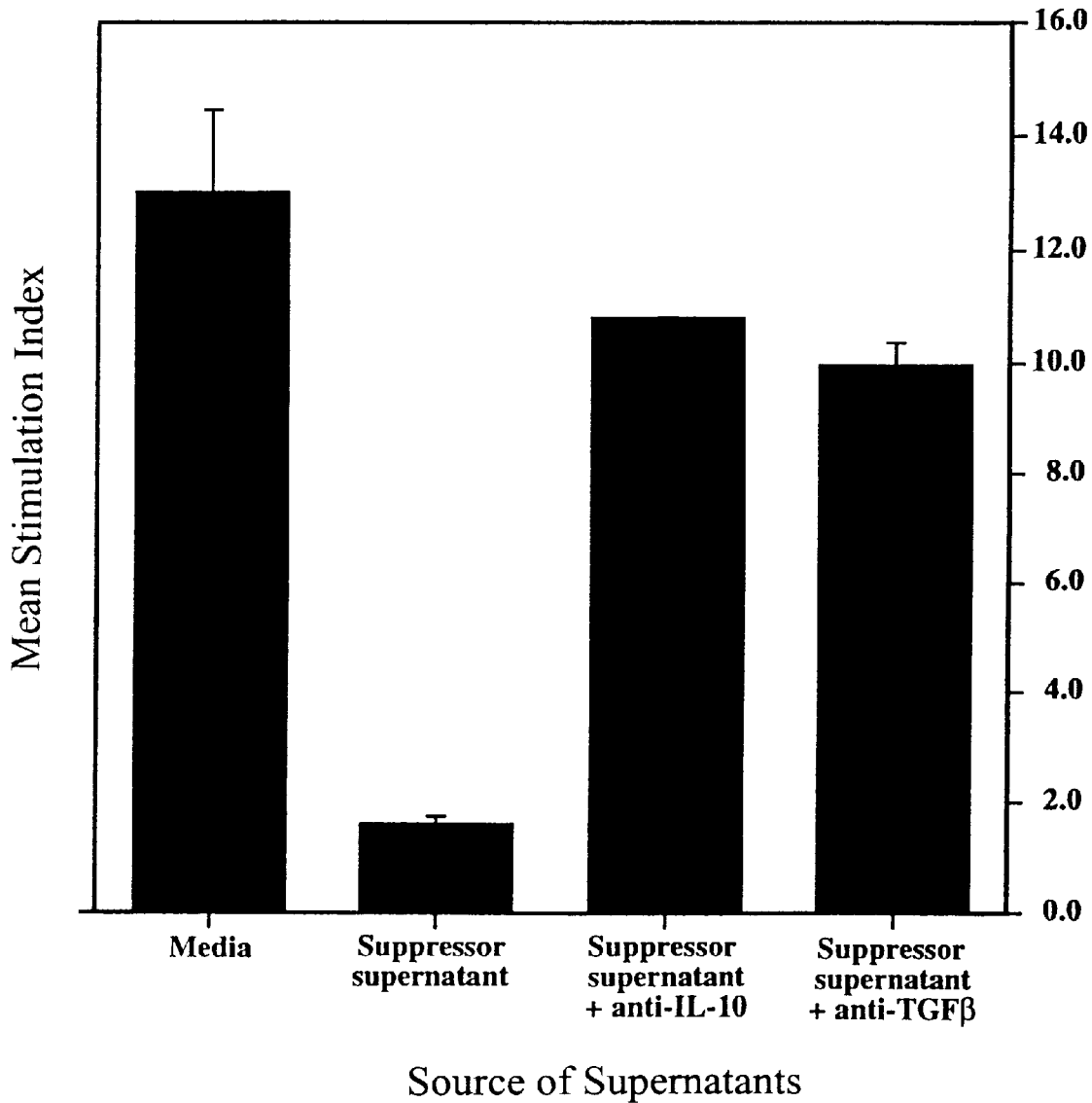

The suppressor factors that IFNτ induced in spleen cells were identified using antibodies to IL-10 and TGF-β. As shown in FIG. 5A, both monoclonal anti-IL-10 and monoclonal anti-TGF-β antibodies blocked the suppressive activity of the suppressor cells on MBP-specific T cell responses. Similarly, both anti-IL-10 and anti-TGF-β antibodies neutralized the suppressive activity of supernatants from IFNτ-induced suppressor cells on the MBP-specific T cell responses (FIG. 5B). Also, addition of the corresponding cytokines in excess reversed the inhibition of suppressive activity induced by IFNτ by the antibodies. The control monoclonal anti-IFNτ antibody had no effect on the suppressor activity of the suppressor cells or their supernatant. Thus, both anti-IL-10 and anti-TGF-β antibodies restored the MBP-induced response to levels comparable to that of the control; this demonstrates a synergistic interaction between IL-10 and TGF-β in inducing suppression of T cell responses.

EXAMPLE 6

Figure 6:
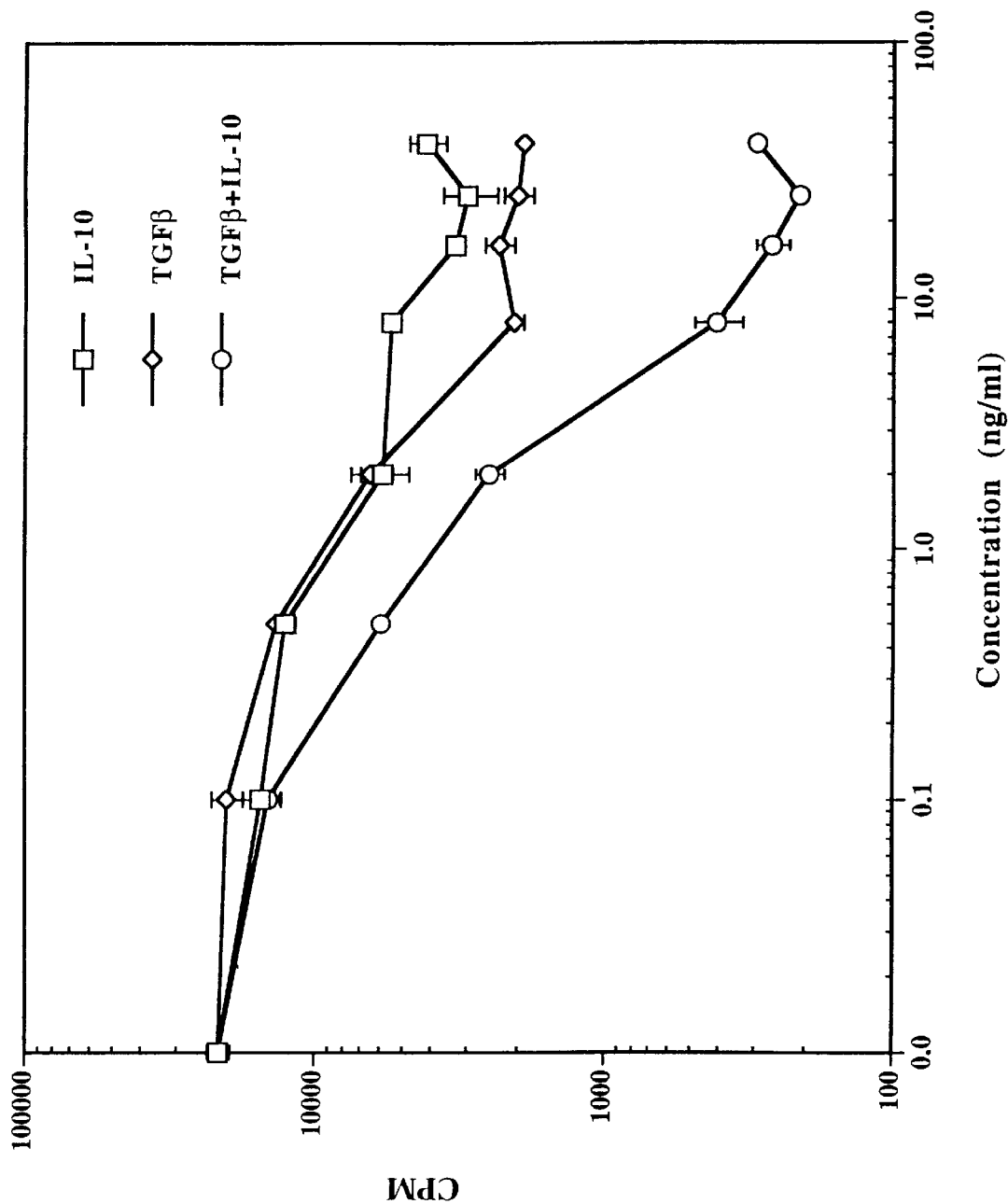
FIG. 6. IL-10 and TGF-β act synergistically to inhibit MBP-specific T cell responses. Varying concentrations of IL-10 and TGF-β individually and together were preincubated with MBP-sensitized mouse spleen cells (5×10$^5$ cells). After 2 h, the cells were stimulated with 30 μg/ml of MBP and incubated for 96 h. Proliferation was assessed by [$^3$H]-thymidine incorporation. Data from one of two representative experiments are presented as CPM±S.D. of quadruplicate cultures. The CPM for unstimulated media treated cells were 6310±911.

IL-10 and TGF-β act synergistically to inhibit MBP-specific T cell responses The synergistic activity of IL-10 and TGF-β on the suppression of MBP-induced mouse spleen cell proliferation was evaluated. As shown in FIG. 6, both IL-10 and TGF-β suppressed MBP-specific T cell responses individually, but IL-10 and TGF-β used together enhanced the suppression of MBP-sensitized spleen cell proliferation in response to MBP in a synergistic fashion. IL-10 and TGF-β administered in combination at a concentration of 8 ng/ml each, greatly reduced MBP-specific responses; this level of reduction is greater than that obtained at 16 ng/ml of each factor administered separately. Thus, the combined effects of IL-10 and TGF-β are greater than simply additive. Accordingly, IL-10 and TGF-β act synergistically at certain concentrations to inhibit MBP-induced EAE spleen cell proliferation.

It should be understood that the examples and embodiments described herein are for illustrative purposes only and that various modifications or changes in light thereof will be suggested to persons skilled in the art and are to be included within the spirit and purview of this application and the scope of the appended claims.

REFERENCES

Blank, M., Krause, I., Buskila, D., Teitelbaum, D., Kopolovic, J., Afek, A., Goldberg, I. and Shoenfeld, Y. (1995) "Bromocriptine immunomodulation of experimental SLE and primary antiphospholipid syndrome via induction of nonspecific T suppressor cells" *Cell. Immunol.* 162:114–122.

Castedo, M., Pelletier, L., Rossert, J., Pasquier, R., Villarroya, H. and Druet, P. (1993) "Mercury-induced autoreactive anti-class II T cell line protects from experimental autoimmune encephalomyelitis by the bias of CD8$^+$ antiergotypic cells in Lewis rats" *J. Exp. Med.* 177:881–889.

Chaouat, G., Assal-Meliani, A., Martal, J., Raghupathy, R., Elliot, J., Mosmann, T. and Wegmann, T. G. (1995) "IL10 prevents naturally occurring fetal loss in the CBA X DBA/2 mating combinations, and local defect in IL10 production in this abortion-prone combination is corrected by in vivo injection of IFNτ" *J Immunol.* 154:4261–4268.

Fleischmann, W. R., Koren, S. and Fleischmann, C. M. (1992) "Orally administered interferons exert their white blood cell suppressive effects via a novel mechanism" *Proc. Soc. Exp. Bio. Med.* 201: 200–207.

Heeke, G. V., Ott, T. L., Strauss, A., Ammaturo, D. and Bazer, F. W. (1996) "High yield expression and secretion of the ovine pregnancy recognition hormone interferon-tau by Pichia pastoris". *J. Interferon Res.* 16:119–126.

Johns, L. T., Flanders, K. C., Ranges, G. E. and Sriram, S. (1991) "Successful treatment of experimental allergic encephalomyelitis with transforming growth factor-β1" *J. Immunol.* 147:1792–1796.

Johnson, H. M. and Blalock, J. E. (1980) "Interferon immunosuppression: mediation by a suppressor factor" *Infect. Immun.* 29:301–305.

Karpus, W. J. and Swanborg, R. H. (1991) "CD4$^+$ suppressor cells inhibit the function of effector cells of experimental autoimmune encephalomyelitis through a mechanism involving transforming growth factor-beta" *J. Immunol.* 146:1163–1168.

Kumar, V., and Sercarz, E. (1994) "Holes in the T cell repertoire to myelin basic protein owing to the absence of the D beta 2-j beta 2 gene cluster: implications for T cell receptor recognition and autoimmunity" *J. Exp. Med.* 179:1637–1643.

Martin, E. W., Remington's Pharmaceutical Science.

Martinotti, A., Stoppacciaro, A., Vagliani, M., Melani, C., Spreafico, F., Wysocka, M., Parmiani, G., Trinchieri, G. and Colombo, M. P. (1995) "CD4 T cells inhibit in vivo the CD8-mediated immune response against murine colon carcinoma cells transduced with interleukin-12 genes" *Eur. J. Immunol.* 25:137–146.

Massague, J. (1990) "The transforming growth factor-β family" *Annu. Rev. Cell. Biol.* 6:597.

Moore, K. W., Vieira, P., Fiorentino, D. F., Trounstine, M. L., Khan, T. A., and Mosmann, T. R., (1990) "Homology of cytokine synthesis inhibitory factor (IL-10) to the Epstein-Barr virus gene BCRF1" *Science* 248:1230.

Mukasa, A., Hiramine, C. and Hojo, K. (1994) "Generation and characterization of a continuous line of CD8$^+$ suppressively regulatory T lymphocytes which downregulates experimental autoimmune orchitis (EAO) in mice" *Clin. Exp. Immunol.* 96:138–145.

Nabozny, G. H., Cobbold, S. P., Waldmann, H. and Kong, Y. L. (1991) "Suppression in murine experimental autoimmune thyroiditis: in vivo inhibition of CD4$^+$ T cell-mediated resistance by a nondepleting rat CD4 monoclonal antibody" *Cell. Immunol.* 138:185–196.

Nouri, A. K. T., Lombard, M. and Williams, R. (1991) "High serum levels of CD8 antigen in primary biliary cirrhosis: a possible cause of suppressor cell dysfunction" *Clin. Exp. Immunol.* 86:140–144.

Pontzer, C. H., Bazer, F. W. and Johnson, H. M. (1991) "Antiproliferative activity of a pregnancy recognition hormone, ovine trophoblast protein-1" *Cancer. Res.* 51: 5304–5307.

Rott, O., Fleischer, B. and Cash, E. (1994) "Interleukin-10 prevents experimental allergic encephalomyelitis in rats" *Eur. J. Immunol.* 24:1434–1440.

Schluesener, H. J. and Lider, O. (1989) "Transforming growth factors β1 and β2: Cytokines with identical immunosuppressive effects and potential role in the regulation of autoimmune T cell function" *J. Neuroimmunol.* 24:249–258.

Smith, H., Sakamoto, Y., Kasai, K. and Tung, K. S. (1991) "Effector and regulatory cells in autoimmune oophoritis elicited by neonatal thymectomy" *J. Immunol.* 147:2928–2933.

Soos, J. M., Subramaniam, P. S., Hobeika, A. C., Schiffenbauer, J. and Johnson, H. M. (1995) "The IFN pregnancy recognition hormone, interferon tau, blocks both development and superantigen reactivation of experimental allergic encephalomyelitis without associated toxicity" *J. Immunol.* 155:2747–2753.

Stevens, D. B., Gould, K. E. and Swanborg, R. H. (1994) "Transforming growth factor-beta 1 inhibits tumor necrosis factor-alpha/lymphotoxin production and adoptive transfer of disease by effector cells of autoimmune encephalomyelitis" *J. Neuroimmunol.* 51:77–83.

Vieira, P., de Waal Malefyt, R., Dang, M. -N., Johnson, K. E., Kastelein, R., Fiorentino, D. F., de Vries, J. E., Roncarolo, M. -G., Mosmann, T. R., and Moore, K. W. (1991) "Isolation and expression of human cytokine synthesis inhibitory factor cDNA clones: homology to Epstein-Barr virus open reading frame BCRFl" *Proc. Natl. Acad. Sci.* 88:1172.

Zamvil, S. S. and Steinman, L. (1990) "The T lymphocyte in experimental allergic encephalomyelitis" *Annu. Rev. Immunol.* 8:579–621.

Zamvil, S S., Al-Sabboagh, A., Nelson, P. A., Kaul, D., Charles, M. S., Mitchell, D J., Steinman, L., Weiner, H. L. and Kuchroo, V. K. 1994. ""Lupus-prone" mice are susceptible to organ-specific autoimmune disease, experimental allergic encephalomyelitis" *Pathobiology* 62:113–119.

We claim:

1. A method for treating Multiple Sclerosis (MS) in a patient in need of such treatment, said method comprising administering a synergistically effective amount of IL-10 and TGF-β, or a biologically active mutein, fragment, variant or peptide thereof, to said patient.

2. The method according to claim 1, wherein said IL-10 and TGF-β are purified.

3. The method according to claim 1, wherein said IL-10 and TGF-β comprise amino acid sequence of human IL-10 and human TGF-β.

4. The method according to claim 1, wherein said method further comprises administering an effective amount of IFNτ.

5. The method according to claim 1, wherein said IL-10 and TGF-β are administered by routes selected from the group consisting of oral administration, parenteral administration, subcutaneous administration, and intravenous administration.

6. The method according to claim 1, wherein said IL-10 and TGF-β are formulated in a pharmaceutically acceptable carrier or excipient.

7. A method for treating MS wherein B cell responses are inhibited in an animal, said method comprising administering a synergistically effective amount of IL-10 and TGF-β, or a biologically active mutein, fragment, variant or peptide thereof, to said animal.

8. The method according to claim 7, wherein said IL-10 and TGF-β are purified.

9. The method according to claim 7, wherein said IL-10 and TGF-β comprise amino acid sequence of human IL-10 and human TGF-β.

10. The method according to claim 7, wherein said method further comprises administering an effective amount of IFNτ.

11. The method according to claim 7, wherein said IL-10 and TGF-β are administered by routes selected from the group consisting of oral administration, parenteral administration, subcutaneous administration, and intravenous administration.

12. The method according to claim 7, wherein said IL-10 and TGF-β are formulated in a pharmaceutically acceptable carrier or excipient.

13. The method according to claim 7, wherein said B cell response is B cell activation or B cell antibody production.

14. A method for treating MS wherein T cell response is inhibited in an animal, said method comprising administering a synergistically effective amount of IL-10 and TGF-β, or a biologically active mutein, fragment, variant or peptide thereof, to said animal.

15. The method according to claim 14, wherein said IL-10 and TGF-β are purified.

16. The method according to claim 14, wherein said IL-10 and TGF-β comprise amino acid sequence of human IL-10 and human TGF-β.

17. The method according to claim 14, wherein said method further comprises administering an effective amount of IFNτ.

18. The method according to claim 14, wherein said IL-10 and TGF-β are administered by routes selected from the group consisting of oral administration, parenteral administration, subcutaneous administration, and intravenous administration.

19. The method according to claim 14, wherein said IL-10 and TGF-β are formulated in a pharmaceutically acceptable carrier or excipient.

20. The method according to claim 14, wherein said T cell response is T cell activation, T cell proliferation, or T cell cytokine production.

* * * * *

UNITED STATES PATENT AND TRADEMARK OFFICE
CERTIFICATE OF CORRECTION

PATENT NO. : 6,083,919

DATED : July 4, 2000

INVENTOR(S) : Howard M. Johnson, Mustafa G. Mujtaba, Jeanne M. Soos

It is certified that error appears in the above-identified patent and that said Letters Patent is hereby corrected as shown below:

Column 6, line 60: "IFNU" should read --IFNτ--.

Column 7, line 54: "orally with IFNR." should read --orally with IFNτ.--.

Signed and Sealed this

Seventeenth Day of April, 2001

*Attest:*

NICHOLAS P. GODICI

*Attesting Officer*     *Acting Director of the United States Patent and Trademark Office*